US00PP14262P39

(12) United States Plant Patent
Boeder

(10) Patent No.: US PP14,262 P3
(45) Date of Patent: Nov. 4, 2003

(54) CHRYSANTHEMUM PLANT NAMED 'MOGUL TIME'

(50) Latin Name: *Dendranthema grandiflora*
Varietal Denomination: Mogul Time

(75) Inventor: Mark Roland Boeder, Den Haag (NL)

(73) Assignee: Cleangro Ltd., Chichester (GB)

( * ) Notice: Subject to any disclaimer, the term of this patent is extended or adjusted under 35 U.S.C. 154(b) by 36 days.

(21) Appl. No.: 09/957,492

(22) Filed: Sep. 19, 2001

(65) Prior Publication Data

US 2003/0056260 P1 Mar. 20, 2003

(51) Int. Cl.[7] ..... A01H 5/00
(52) U.S. Cl. ..... Plt./286

(58) Field of Search ..... Plt./286

(56) References Cited

U.S. PATENT DOCUMENTS

PP8,179 P 3/1993 VandenBerg ..... Plt./74.1

OTHER PUBLICATIONS

First date of sale or offer of sale for variety 'Mogul Time,' direct to a buyer outside the United States, Jan. 1, 2000.

*Primary Examiner*—Bruce R. Campell
*Assistant Examiner*—Michelle Kizilkaya

(57) ABSTRACT

A new variety of Chrysanthemum plant named 'Mogul Time,' having an upright and branching habit of medium/tall vigor and attractive daisy flowers with purple/silver tubular spoon petals.

1 Drawing Sheet

Latin name of the genus and species: Botanical classification: *Dendranthema grandiflora.*

Variety denomination: The new Chrysanthemum variety denomination is 'Mogul Time.'

BACKGROUND OF THE INVENTION

The present invention comprises a new and distinct cultivar of Chrysanthemum botanically known as *Dendranthema grandiflora,* and referred to by the cultivar name 'Mogul Time.'

'Mogul Time,' identified as 20357-0 originated from a cross made by Mark Boeder, in a controlled breeding program in Chichester, West Sussex, United Kingdom. The female parent of the new variety is known as P333C6, and the male parent is the variety known as P333C5. The new variety 'Mogul Time' has been asexually reproduced by vegetative cuttings at Chichester, West Sussex, United Kingdom and the distinguishing characteristics are retained through successive generations of asexual reproduction.

BRIEF SUMMARY OF THE INVENTION

'Mogul Time' is a pot type of Chrysanthemum plant variety having slightly cupped circular flowers with spoon shaped purple/white flowers, with a slightly domed capitulum and daisy type flowers.

Comparison with Parent

Plants of the new Chrysanthemum variety 'Mogul Time' are similar to the parent cultivar P333C6 in plant habitat and growth rate. In side-by-side comparisons in Chichester, West Sussex, United Kingdom, under commercial practice, plants of the new Chrysanthemum variety 'Mogul Time' differed from plants of the parent cultivar P333C6 in the following characteristics.

1. The new variety 'Mogul Time' produces purple colour spoon style flowers, whereas the parent cultivar P333C6 produces purple and white daisy flowers.
2. Plants of the new variety 'Mogul Time' have larger and shorter inflorescence than plants of the parent cultivar P333C6.
3. 'Mogul Time' has silver inflorescence reverse to the fluted section of the spoon effect.

Comparison with Other Varieties

Plants of the new Chrysanthemum variety 'Mogul Time' are similar to the cultivar 'Rapture' (U.S. Plant Pat. No. 8,179) in plant habitat and growth rate. However, in side-by-side comparisons in Chichester, West Sussex, United Kingdom, under commercial practice, plants of the new Chrysanthemum variety 'Mogul Time' compared to plants of the cultivar 'Rapture' in the following characteristics.

1. The new variety 'Mogul Time' produces purple and silver spoon daisy colour flowers, whereas the cultivar 'Rapture' produces purple spoon daisy colour flowers.
2. Plants of the new variety 'Mogul Time' have smaller and shorter inflorescence than plants of the cultivar 'Rapture.'
3. The new variety 'Mogul Time' has more vigour than 'Rapture.' 'Rapture' has two days faster response time than 'Mogul Time.'

BRIEF DESCRIPTION OF ILLUSTRATIONS

Typical specimens of the plant and flowers for the new Chrysanthemum variety 'Mogul Time' are shown in the accompanying photograph. The colours shown are as true as possible within the usual limits of this kind of illustration.

FIG. 1 is a whole plant view of the new variety 'Mogul Time' grown in a pot. The plant shown in the illustration is 60 days from start of Short Days.

DETAILED BOTANICAL DESCRIPTION

The following description of the new Chrysanthemum variety 'Mogul Time' is of plants grown in a greenhouse in Chichester, West Sussex, United Kingdom in the month of August. The cultivar has not been observed under all possible environmental conditions. The phenotype may vary significantly with variations in the environment such as temperature, length of day and light intensity, without any variance in genotype. The commercial classification of the new variety is a pot Chrysanthemum.

Plants of the new variety have been grown successfully under temperature conditions averaging about 18° C. at night and about 24° C. to 25° C. during the day under light conditions of about 5,000 to 6,000 foot candles. The plants respond well to the use of growth retardant, such as three B9 treatments at about 2500 ppm. To produce a commercial product the plants may be pinched once with the center bud removed. The typical container size for commercial growth is 14 cm. It has been observed that the shelf life of the new variety is about 24 days with a response time of about 8½ weeks. The new variety is suitable for growth in a temperature range of 16° C. to 25° C.

The new variety may be produced as a Spray or disbud. The following description is with respect to a plant produced as Spray pot Chrysanthemums. In the description of this new Chrysanthemum variety, colour values have been taken from The Royal Horticultural Society Colour Chart (R.H.S.C.C.).

Plant

Plant type: Pot.
Habit: Upright and branching.
Height: Medium/Tall (20 to 25 cm).
Width: Near 28 cm.
Branching characteristics: Upright and spreading.
Length of lateral branches: 12 to 18 cm.
Number of breaks from pinch: 4 to 6.
Stem colour: 138 B.
Response time: 54 days.
Vigour: Medium/Tall.
Shelf life: Near 22 to 23 days.
Disease (susceptibility/resistance observed): None observed to date.
Pest (susceptibility/resistance observed): None Observed to date.
Drought/temperature resistance: None observed to date.
Growth retardant type and treatment: B9 85% 3 applications of 2.5 gram/liter at 2 days, 21 days and 31 days, after propagating unrooted vegetative cuttings.
The plants were grown for two weeks in Long Day conditions (20 hours of light) and then transferred to Short Day conditions (13 hours of dark).
Propagation:
*Type.*—Vegetative propagation via stem cuttings.
*Time to rooting.*—10–12 days with soil temperatures of 18° C.
*Rooting habit.*—Fine and fibrous.

Foliage

Number of leaves per lateral branch: 7 to 11.
Compound or single: Single.
Arrangement of leaves: Alternate.
*Shape of leaf.*—Typically 5 lobed, oblong ovate.
*Size of leaf.*—Width (cm): Near 4½ cm. Length (cm): Near 8 cm.
*Leaf apex.*—Acute.
*Base.*—Obtuse.
*Attachment.*—Petioled.
*Aspect.*—Slightly undulating.
*Margin.*—Palmately lobed.
*Surface characteristics.*—Top: Pubescent. Bottom: Pubescent.
Petiole:
*Colour.*—Near 137 C.
*Length.*—Near 1½ cm.
Venation: Net prominent mid and lateral veins at under side.
*Colour.*—Upper side: Near 138 A. Under side: Near 138 C.
Colour:
*Mature leaf, upper side.*—Near 139 A; under side: Near 137 C.
*Young leaf, upper side.*—Near 137 A; under side: Near 137 C.

Flower

Flower appearance: Cupped, circular.
Flower type: Single (Daisy).
Flower form: Cupped.
Flower shape: Circular.
Flower habit: Upright.
Number of blossoms per branch: 5 to 8.
Inflorescence form: Cyme.
*Depth of fully expanded blossoms.*—Near 2 cm.
*Diameter of fully expanded blossoms.*—Near 7 cm.
Phyllaries:
*Number.*—18 to 24.
*Colour.*—Near 137 B.
*Length.*—Near 1.2 cm.
*Width.*—Near 0.2 cm.
*Texture/appearance.*—Pubescent.
Peduncles: Peduncle length is shortest at the terminal flower and progressively longer moving down the stem.
*Length.*—12 cm (average).
*Colour.*—Near 137 B.
*Surface.*—Slightly pubescent.
*Habit.*—Slightly undulating.
*Strength.*—Medium.
Pedicel:
*Length.*—Terminal: Near 5 cm; Lateral: Near 7 cm.
*Colour.*—Near 137 B.
*Surface.*—Slightly pubescent.
*Habit.*—Slightly undulating.
*Strength.*—Medium.
Ray florets:
*Form/shape.*—Tubular spooned.
*Texture/appearance.*—Matte.
*Number per flower.*—22 to 30.
*Length.*—Near 2.8 cm; Width: Tube near 0.3 average; Spoon near 0.5 average.
*Apex.*—Rounded.
*Base.*—Tapered.
*Margin.*—Entire.
Disc florets:
*Form/shape.*—Cylindrical.
*Texture/appearance.*—Shiny.
*Number per flower.*—150 to 200.
*Length.*—Near 0.4 to 0.5 cm; Width: 0.1 cm.
*Diameter of disc.*—Near 1.1 cm.
Fragrance: Slight.
Flower bud (at onset of colour):
*Length.*—Near 0.8 cm.
*Diameter.*—Near 0.2 cm.

*Form/shape.*—Globular, pear shaped.

General flower colour: Purple and silver.

1. *Ray florets, upper side.*—Immature: Near 63 A. Mature: Near 63 A. Older/Fading: Near 63 A.
2. *Ray florets, under side.*—Immature: Near 155 C. Mature: Near 155 C. Older/Fading: Near 155 C.
3. *Disc florets.*—Immature: Near 143 C. Mature: Near 14 A. Older/Fading: Near 14 B.
4. *Bud.*—Near 138 B.

Flower progression: Flowers hold colour and form well during aging.

Other distinguishing characteristics: Spoon petals with silver flute.

Reproductive Organs

Gynoecium present on ray and disc florets:

*Pistil number on ray florets.*—30 to 35.

*Pistil number on disc florets.*—Approx. 80.

*Stigma color.*—Near 6C.

*Stigma shape.*—Forked.

*Style color.*—Near 6C.

*Style length.*—0.3 cm.

Androecium present on disc florets only:

*Stamen number.*—>*100* when observed.

*Anther shape.*—Cylindrical.

*Anther color.*—Near 7A.

*Pollen color.*—Near 14A.

*Pollen quantity.*—Little.

Fruit and seeds: None observed.

What is claimed is:

1. A new and distinct variety of Chrysanthemum plant, substantially as described and illustrated herein.

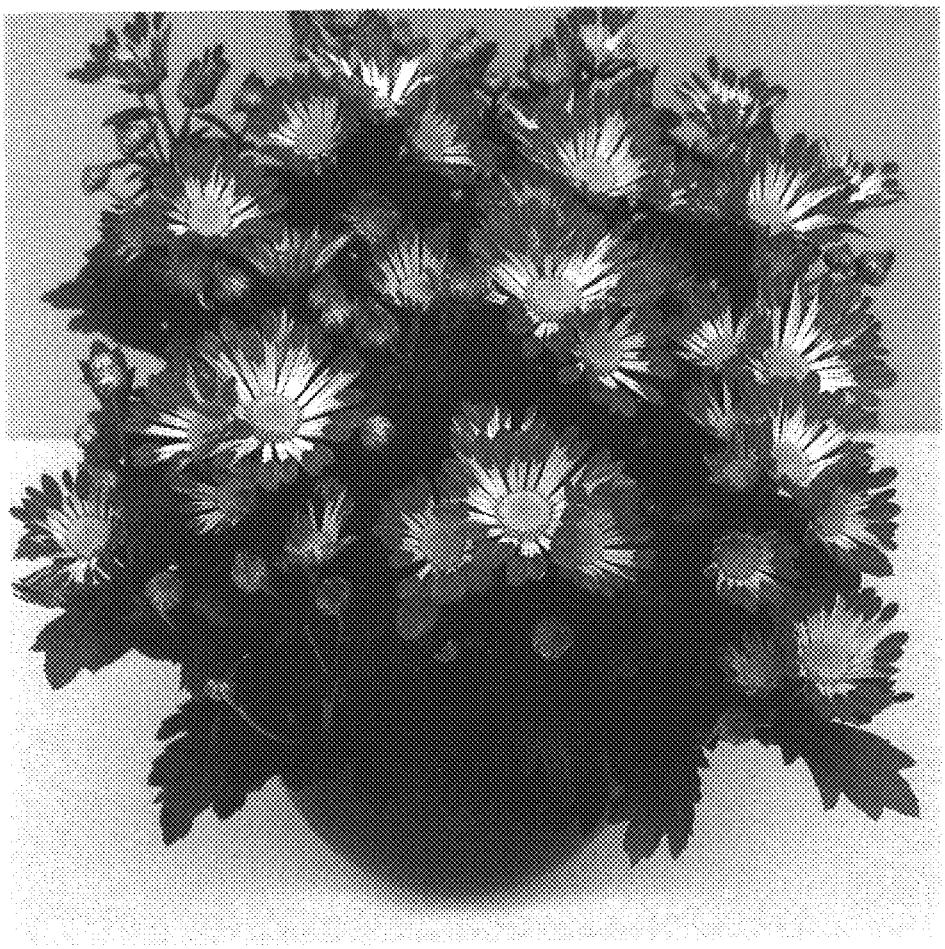

* * * * *